United States Patent

Rozental et al.

(10) Patent No.: US 11,592,542 B2
(45) Date of Patent: Feb. 28, 2023

(54) CODED APERTURE ULTRASOUND DETECTOR

(71) Applicant: TECHNION RESEARCH & DEVELOPMENT FOUNDATION LIMITED, Haifa (IL)

(72) Inventors: Amir Rozental, Haifa (IL); Evgeny Hahamovich, Mitzpe Aviv (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 178 days.

(21) Appl. No.: 17/030,615

(22) Filed: Sep. 24, 2020

(65) Prior Publication Data

US 2021/0088640 A1 Mar. 25, 2021

Related U.S. Application Data

(60) Provisional application No. 62/904,775, filed on Sep. 24, 2019.

(51) Int. Cl.
*G01S 7/52* (2006.01)
*A61B 8/08* (2006.01)
*G01S 15/89* (2006.01)

(52) U.S. Cl.
CPC ........ *G01S 7/52093* (2013.01); *A61B 8/5223* (2013.01); *G01S 15/8959* (2013.01)

(58) Field of Classification Search
CPC ............. G01S 7/52093; G01S 15/8959; G01S 15/8925; G01S 15/8927; A61B 8/5223; A61B 8/15; A61B 8/4483; A61B 8/4488; A61B 8/5207
See application file for complete search history.

(56) References Cited

U.S. PATENT DOCUMENTS

| 2013/0286778 A1* | 10/2013 | Kisner | G01S 15/89 367/87 |
| 2016/0331353 A1* | 11/2016 | Ralston | A61B 8/546 |
| 2018/0080822 A1* | 3/2018 | Lau | G01J 3/2889 |

FOREIGN PATENT DOCUMENTS

| CN | 102822661 A | * 12/2012 | A61B 5/0095 |
| WO | WO-2016058769 A1 | * 4/2016 | G01J 1/0437 |

OTHER PUBLICATIONS

Pieter Kruizinga et al., Compressive 3D ultrasound imaging using a single sensor (Dec. 8, 2017), Science Advances, 3, e1701423, pp. 1-11 (Year: 2017).*

(Continued)

*Primary Examiner* — Joseph M Santos Rodriguez
*Assistant Examiner* — Kaitlyn E Sebastian
(74) *Attorney, Agent, or Firm* — The Roy Gross Law Firm, LLC; Roy Gross

(57) ABSTRACT

An ultrasound detection device comprising: an ultrasound receiver configured to generate a signal indicative of a pressure of ultrasound that impinges on the receiver; and a coded mask comprising an ultrasound-blocking material perforated by an array of a plurality of apertures, the apertures arranged such that when the coded mask is placed over the receiver between the receiver and a source of ultrasound in a predetermined lateral position, the ultrasound is transmitted from the ultrasound source to the receiver via a known unique pattern of active apertures of the plurality of apertures such that the signal that is generated by the receiver is a multiplexed signal.

18 Claims, 14 Drawing Sheets

(56) References Cited

OTHER PUBLICATIONS

Harwit, M., & Sloane, N. J. A. (1979). Hadamard Transform Optics. Academic Press, https://doi.org/10.1016/8978-0-12-330050-8.X5001-X.

Hahamovich, E., & Rosenthal, A. (2020). Ultrasound Detection Arrays Via Coded Hadamard Apertures. IEEE Transactions on Ultrasonics, Ferroelectrics, and Frequency Control, 67(10), 2095-2102. DOI: 10.1109/TUFFC.2020.2993583.

Nachappa Gopalsami, Shaolin Liao, Thomas W. Elmer, Eugene R. Koehl, Alexander Heifetz, Apostolos Paul C. Raptis, Leonidas Spinoulas, and Aggelos Katsaggelos "Passive millimeter-wave imaging with compressive sensing," Optical Engineering 51(9), 091614 (Sep. 14, 2012). https://doi.org/10.1117/1.OE.51.9.091614.

Shen, H., Gan, L., Newman, N., Dong, Y., Li, C., Huang, Y., & Shen, Y. C. (2012). Spinning disk for compressive imaging. Optics letters, 37(1), 46-48. https://doi.org/10.1364/OL.37.000046.

Hahamovich E, Rosenthal A. Ultrasound Detection Using Acoustic Apertures. IEEE Trans Ultrason Ferroelectr Freq Control. Jan. 2018;65(1):120-126. doi: 10.1109/TUFFC.2017.2773570. PMID: 29283354.

E. Hahamovich, S. Monin, Y. Hazan, M. Nagli, and A. Rosenthal "3D optoacoustic tomography via coded acoustic apertures", Proc. SPIE 11642, Photons Plus Ultrasound: Imaging and Sensing 2021, 116420D (Mar. 5, 2021); https://doi.org/10.1117/12.2576986.

\* cited by examiner

CODED APERTURE ULTRASOUND DETECTOR

CROSS REFERENCE TO RELATED APPLICATIONS

This application claims the benefit of priority of U.S. Provisional Patent Application No. 62/904,775 filed on Sep. 24, 2019, the contents of which are incorporated herein by reference in its entirety.

FIELD OF THE INVENTION

The present invention, in some embodiments thereof, relates to ultrasound detectors and, more particularly, but not exclusively, to an ultrasound detector with a coded aperture.

BACKGROUND OF THE INVENTION

Technologies for the generation and detection of ultrasound have numerous applications in the biomedical fields as well in the field of nondestructive testing. For example, optoacoustic imaging may be utilized to examine biological tissues. In optoacoustic imaging, a region of tissue may be irradiated by laser pulses so as to cause heating and thermal expansion of the tissue. The expansion of the tissue may generate ultrasound that may be detectable by one or more detectors. In some cases, one or more tomographic reconstruction techniques may be applied to detected ultrasound signals so as to map one or more properties of the irradiated tissue.

SUMMARY OF THE INVENTION

The following embodiments and aspects thereof are described and illustrated in conjunction with systems, tools and methods which are meant to be exemplary and illustrative, not limiting in scope.

There is provided, in an embodiment, an ultrasound detection device comprising: an ultrasound receiver configured to generate a signal indicative of a pressure of ultrasound that impinges on the receiver; and a coded mask comprising an ultrasound-blocking material perforated by an array of a plurality of apertures, the apertures arranged such that when the coded mask is placed over the receiver between the receiver and a source of ultrasound in a predetermined lateral position, the ultrasound is transmitted from the ultrasound source to the receiver via a known unique pattern of active apertures of the plurality of apertures such that the signal that is generated by the receiver is a multiplexed signal.

There is also provided in an embodiment, an ultrasound detection method comprising: placing a coded mask relative to an ultrasound receiver in a predetermined lateral position, the coded mask comprising an ultrasound blocking material perforated by an array of a plurality of apertures, the apertures arranged such that the ultrasound is transmitted from an ultrasound source to the receiver via a unique pattern of active apertures of the plurality of apertures; operating the ultrasound receiver to acquire a multiplexed signal; and processing the acquired multiplexed signals to recover a signal of interest.

In some embodiments, the coded mask is laterally translatable relative to the receiver to a plurality of predetermined lateral positions.

In some embodiments, the number of active apertures via which the ultrasound is transmitted to the receiver is identical at each of the plurality of predetermined lateral positions.

In some embodiments, the coded mask and the receiver are laterally translatable together to a plurality of lateral positions, and wherein the coded mask remains stationary relative to the receiver during the translating.

In some embodiments, the plurality of apertures are arranged along at least one axis, and wherein the separation distance between any pair of the apertures along each of the at least one axis is substantially equal to an integral multiple of a minimum separation distance between adjacent apertures of the plurality of apertures.

In some embodiments, the plurality of apertures are arranged along the at least one axis such that when the coded mask is divided along each of the at least one axis into a plurality of elements, the length of each of the elements is substantially equal to the minimum separation distance, and wherein the pattern of the active apertures within those elements of the coded mask that cover the receiver corresponds to values in a row of weighting matrix in the form of a cyclic S matrix.

In some embodiments, the plurality of apertures are arranged in a two-dimensional array.

In some embodiments, the device further comprises a processor that is configured to process, and the method further comprises processing, the multiplexed signals to recover an acoustic signal of interest, and wherein the processor is configured to process the multiplexed signals by applying an inverse of a weighting matrix that corresponds to the unique patterns of the active apertures.

There is further provided, in an embodiment, an ultrasound detection device comprising: an ultrasound receiver configured to generate a signal indicative of a pressure of ultrasound that impinges on the receiver; and a coded mask comprising a phase-shifting material and including an array of elements, some of the elements including an aperture, wherein ultrasound that traverses an element of the array of elements that includes an aperture has a phase that is inverted relative to a phase of ultrasound that traverses an element of the array of elements that does not include an aperture, the elements arranged such that when the coded mask is placed over the receiver between the receiver and a source of ultrasound in a predetermined lateral position, the ultrasound is transmitted from the ultrasound source to the receiver via a known unique pattern of active apertures of the plurality of apertures such that the signal that is generated by the receiver is a multiplexed signal.

There is provided, in accordance with an embodiment of the invention, an ultrasound detection device including: an ultrasound receiver configured to generate a signal indicative of a pressure of ultrasound that impinges on the receiver; and a coded mask including an ultrasound-blocking material perforated by an array of a plurality of apertures, the apertures arranged such that when the mask is placed over the receiver between the receiver and a source of ultrasound, and when the mask is laterally translated relative to the receiver to each of a plurality of predetermined lateral positions, the ultrasound is transmitted from the ultrasound source to the receiver via a known unique pattern of active apertures of the plurality of apertures such that the signal that is generated by the receiver is a multiplexed signal.

Furthermore, in accordance with an embodiment of the invention, the number of active apertures via which the ultrasound is transmitted to the receiver is identical at each of the plurality of predetermined lateral positions.

Furthermore, in accordance with an embodiment of the invention, the device further includes a motorized translation unit for laterally translating the mask to each of the predetermined positions.

Furthermore, in accordance with an embodiment of the invention, the plurality of apertures are arranged along a single axis, the separation distance between any pair of the apertures being substantially equal to an integral multiple of a minimum separation distance between adjacent apertures of the plurality of apertures.

Furthermore, in accordance with an embodiment of the invention, the plurality of apertures are arranged along the axis such that when the mask is divided along the axis into a plurality of elements, the length of each of the elements being substantially equal to the minimum separation distance, at each of the predetermined lateral positions of the mask the pattern of the active apertures within those elements of the mask that cover the receiver corresponds to values in a row of weighting matrix in the form of a cyclic S matrix.

Furthermore, in accordance with an embodiment of the invention, the plurality of apertures are arranged in a two-dimensional array.

Furthermore, in accordance with an embodiment of the invention, the device includes a processor that is configured to process the multiplexed signals to recover an acoustic signal of interest.

Furthermore, in accordance with an embodiment of the invention, the processor is configured process the multiplexed signals by applying an inverse of a weighting matrix that corresponds to the unique patterns of the active apertures at the plurality of predetermined lateral positions.

There is further provided, in accordance with an embodiment of the invention, an ultrasound detection method including: sequentially laterally translating a coded mask relative to an ultrasound receiver to each of a plurality of predetermined lateral positions, the mask including an ultrasound blocking material perforated by an array of a plurality of apertures, the apertures arranged such that when the mask is positioned at each of the lateral positions, the ultrasound is transmitted from an ultrasound source to the receiver via a unique pattern of active apertures of the plurality of apertures; operating the ultrasound receiver to acquire a multiplexed signal when the mask is at each of the predetermined positions; and processing the acquired multiplexed signals to recover a signal of interest.

Furthermore, in accordance with an embodiment of the invention, the signal of interest is proportional to pressure of the ultrasound that impinges on an aperture of the plurality of apertures.

Furthermore, in accordance with an embodiment of the invention, the plurality of apertures are arranged along a single axis, the separation distance along the axis between any pair of the apertures being substantially equal to an integral multiple of a minimum separation distance between adjacent apertures of the plurality of apertures.

Furthermore, in accordance with an embodiment of the invention, sequentially laterally translating the mask includes translating the mask along the single axis, the displacement of each translation being substantially equal to the minimum separation distance.

Furthermore, in accordance with an embodiment of the invention, processing the multiplexed signals includes applying an inverse of a weighting matrix to the multiplexed signals.

Furthermore, in accordance with an embodiment of the invention, when the plurality of apertures are arranged along a single axis, each weight value in a row of the weighting matrix is indicative of the presence or absence of an active aperture in an active element of the mask that is located between the ultrasound source and the receiver when the mask is at one of the predetermined lateral positions of the mask, a width of each active element being substantially equal to a minimum separation between two of the apertures along the axis, and wherein the weight values in each successive row of the weighting matrix correspond the presence or absence of active apertures in each successive predetermined lateral position of the mask.

Furthermore, in accordance with an embodiment of the invention, the weighting matrix includes a cyclic S matrix whose order is equal to the number of the predetermined lateral positions of the mask.

Furthermore, in accordance with an embodiment of the invention, a value in a row of the weighting matrix that corresponds to the presence of an active aperture is 1, and a value in a row of the weighting matrix that corresponds to the absence of an active aperture is 0.

Furthermore, in accordance with an embodiment of the invention, the ultrasound source includes heated biological tissue.

There is further provided, in accordance with an embodiment of the invention, an ultrasound detection device including: an ultrasound receiver configured to generate a signal indicative of a pressure of ultrasound that impinges on the receiver; and a coded mask including a phase-shifting material and including an array of elements, some of the elements each including an aperture, wherein ultrasound that traverses an element of the array of elements that includes an aperture has a phase that is inverted relative to a phase of ultrasound that traverses an element of the array of elements that does not include an aperture, the elements arranged such that when the mask is placed over the receiver between the receiver and a source of ultrasound, and when the mask is laterally translated relative to the receiver to each of a plurality of predetermined lateral positions, the ultrasound is transmitted from the ultrasound source to the receiver via a known unique pattern of active apertures of the plurality of apertures such that the signal that is generated by the receiver is a multiplexed signal.

Furthermore, in accordance with an embodiment of the invention, the plurality of apertures are arranged along a single axis, the separation distance between any pair of the apertures being substantially equal to an integral multiple of a minimum separation distance between adjacent apertures of the plurality of apertures.

Furthermore, in accordance with an embodiment of the invention, the plurality of apertures are arranged along the axis such that when the mask is divided along the axis into a plurality of elements, the length of each of the elements being substantially equal to the minimum separation distance, at each of the predetermined lateral positions of the mask the pattern of the active apertures within those elements of the mask that cover the receiver corresponds to values in a row of weighting matrix in the form of a Hadamard matrix, wherein a value in a row of the weighting matrix that corresponds to the presence of an active aperture is 1, and a value in a row of the weighting matrix that corresponds to the absence of an active aperture is −1.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION OF THE INVENTION

Figure 1A:
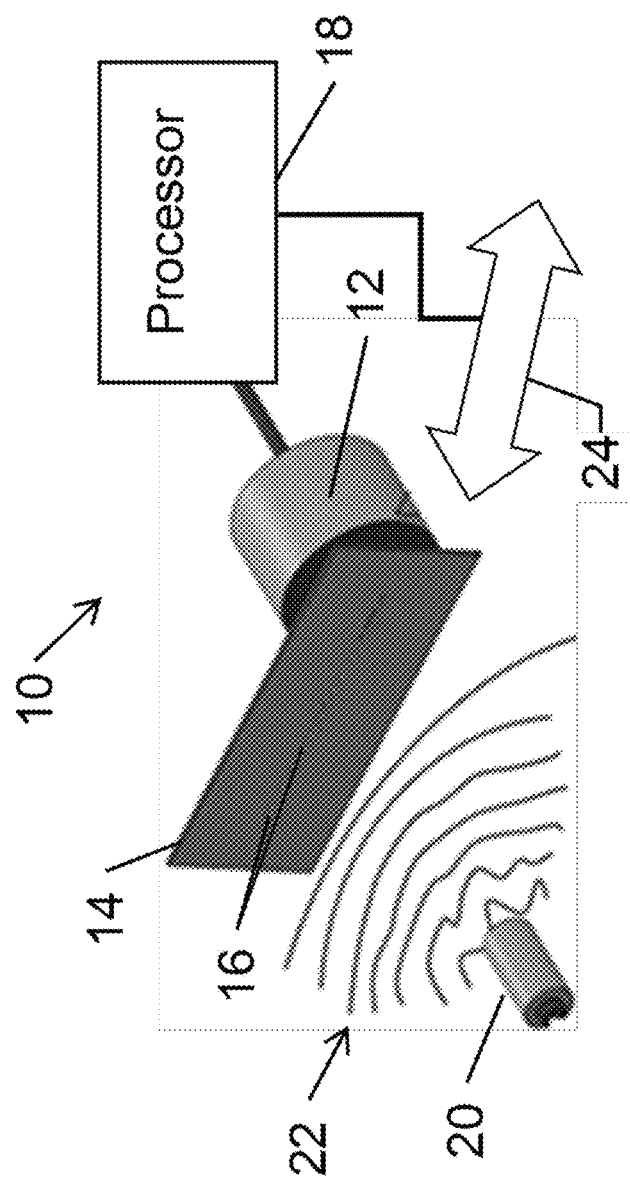
FIG. 1A schematically illustrates a one-dimensional coded aperture ultrasound detector, in accordance with an embodiment of the present invention.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In accordance with an embodiment of the present invention, a coded aperture ultrasound detector includes an ultrasound receiver component and a coded mask that is located between a source of the ultrasound that is to be detected and the receiver. In some embodiments, the coded mask has a fixed position and is stationary relative to the receiver. In some embodiments, the coded mask and the receiver are laterally translatable together, while the coded mask remains stationary relative to the receiver. In some embodiments, the coded mask is laterally movable in one or more axes across the receiver to a predetermined number of different predetermined lateral positions relative to the receiver. At each lateral position, a different portion of the mask is located between the ultrasound source and the receiver. As used herein, lateral movement of the coded mask relative to the receiver refers to motion that is substantially parallel to that surface of the receiver that is sensitive to impinging ultrasound. When ultrasound impinges on the sensitive surface (there may be more than one), the receiver generates an electrical or other signal that is indicative of the pressure of the impinging ultrasound. The portion of the mask that is located between the ultrasound source and the receiver when a measurement is acquired is herein referred to as being in front of the receiver or covering the receiver.

The coded mask includes an ultrasound-blocking material that is perforated with an array of ultrasound apertures at known locations on the mask. Thus, ultrasound that is emitted by an ultrasound source may be transmitted to the receiver via those apertures that are positioned in front of an ultrasound-sensitive region of the receiver. The array is configured such that when positioned at each of the predetermined lateral positions, the ultrasound is transmitted to the receiver via a unique spatial pattern of the ultrasound apertures relative to the receiver. Therefore, when the ultrasound that is emitted by the ultrasound source is substantially constant for each measurement, differences among the signals that are generated by the receiver at the different lateral positions may be attributed to the different patterns of the apertures, and to random noise. For example, random noise may be produced by the ultrasound source, by the receiver, and by electronics or electrical circuitry.

The ultrasound receiver of the coded aperture ultrasound detector includes an ultrasound sensor that is configured to generate an electric signal that is indicative of the pressure of ultrasound that impinges on the detection device. For example, the ultrasound sensor may include a piezoelectric transducer, e.g., that includes a piezoelectric material such as polyvinylidene fluoride (PVDF) or another piezoelectric material, that generates an electrical signal when subjected to ultrasound. In typical medical applications, the ultrasound may have wavelengths within the range of about 0.1 mm to about one millimeter, or another suitable range.

The coded mask is constructed of a material that blocks ultrasound. The ultrasound-blocking material may reflect, scatter, or absorb the ultrasound. For example, the mask may include urethane foam (e.g., PORON™), or another absorbent material. The mask may include a high impedance material such as stainless steel or a similar high impedance or reflective material. When necessary, the absorbent material may be mounted on a backing surface in order to provide sufficient stiffness to enable the mask to retain its shape when in use. For example, the backing material may include polymethyl methacrylate (PMMA) or another polymer, or another organic or inorganic material that may provide stiffness to the coded mask.

The coded mask is perforated by a one-dimensional or two-dimensional array of apertures. Therefore, ultrasound may be transmitted through the mask only via the apertures. Typically, the diameter or another characterizing dimension of each aperture is approximately equal to, or on the order of, a characteristic wavelength of the ultrasound that is to be detected. Accordingly, ultrasound that passes through one of the apertures may spread as a result of diffraction. Therefore, a maximum distance between the mask and the receiver surface may be limited in order to limit the diffractive spreading of the ultrasound over the detector. For example, the distance may be limited such that a spreading angle of the ultrasound that emerges through the aperture (e.g., defined by the full width at half maximum, or by another suitable metric) is limited to a spreading angle in the range of about 20° to about 30°, or to another suitable range.

Typically, the surface of the mask may be considered to be divided into a predetermined number of contiguously arranged elements of approximately equal size. For example, the elements may be arranged linearly along at least one axis of the mask, or two-dimensionally over the surface of the mask. Some of the elements include apertures that may transmit ultrasound. Others of the elements do not include apertures, and are thus opaque to ultrasound. The spacing between adjacent elements along each of the at least one axis of the mask, is typically equal to a minimum distance between adjacent apertures along that axis, may be selected so as to limit crosstalk between regions of the receiver that are covered by adjacent elements to a predetermined maximum value. Such crosstalk may occur, for example, when diffractive or other spreading of ultrasound that is transmitted by an aperture in one element reaches a region of the receiver that is covered by an adjacent or neighboring element. A maximum value of the crosstalk may be expressed, for example, as a value that is proportional to the pressure of ultrasound that is transmitted by an aperture and that spreads to a region of the receiver that is adjacent to, or neighbors, the region that is covered by that aperture. For example, the maximum value may be expressed as a fraction or percentage of the ultrasound pressure that is incident on the aperture, or is incident on the region of the receiver directly behind the aperture, or another ultrasound pressure that is related to, or indicative of, this impinging or directly transmitted ultrasound pressure.

As another example, some elements of the mask (e.g., that contain apertures) may transmit the ultrasound with one phase, while other elements of the mask (e.g., that lack apertures) may transmit the ultrasound with an opposite inverted phase. For example, rather than including an absorbent or reflecting material, the mask may include only a backing material (e.g., PMMA or another material). A phase shift may be effected by selection of the thickness of the backing material in each element of the mask.

In a typical configuration for use of the coded aperture ultrasound detector, the ultrasound receiver of the ultrasound detector remains stationary relative to an ultrasound source. A typical ultrasound source may include tissue that is heated by radiation, such as by a pulsed laser beam or by another source of absorbable radiation, so as to expand and generate ultrasound waves. In some embodiments, the coded mask has a fixed position and is stationary relative to the receiver. In some embodiments, the configuration may include a translation mechanism that is configured to translate the mask laterally across the receiver. For example, the translation mechanism may include one or more controllable electric motors, e.g., stepper motors or other types of motors, that may be operated to translate the mask to a sequence of predetermined lateral positions relative to the receiver. A control mechanism may include one or more encoders, distance or proximity sensors, or other components to enable measurement or verification of a position of the mask relative to the receiver.

Typically, the lateral dimensions of the mask are larger than the corresponding dimensions of the receiver. Thus, at each allowed lateral position of the mask, the receiver is covered by the mask, and ultrasound may reach the receiver only via apertures of the mask. Also typically, at each lateral position of the mask, only a fraction of the apertures are located between the ultrasound source and the receiver, and thus transmit ultrasound to the receiver, while remaining apertures are located to the sides of the receiver. An aperture via which the ultrasound is transmitted from the source to the receiver at a current lateral position of the mask is herein referred to as an active aperture. Similarly, any mask element, with or without an aperture, that, at a current lateral position of the mask, is located between the ultrasound source and the receiver (e.g., such that if that mask element were to include an aperture, that aperture would function as an active aperture) is herein referred to as an active element. An active element is referred to herein as covering the mask, whereas the remaining elements do not.

A pattern of the distribution of apertures over the mask is designed such that at each predetermined lateral position to which the mask is translated, the pattern of apertures that covers the receiver is unique. Thus, at each different lateral position of the mask, the ultrasound is transmitted from the ultrasound source to the receiver via a pattern of active apertures that is distinguishable from the pattern of active apertures at any other of the predetermined lateral positions. In some cases, the pattern of active apertures may be cyclical such as to repeat after a predetermined number of the sequential lateral translations.

The signal that is produced by the receiver at each of the predetermined positions is a spatially multiplexed signal. At a given time, the produced signal may be considered to include a term that is proportional to a weighted sum of the ultrasound pressure that results from concurrent transmission of the ultrasound via all of the active apertures of the active elements of the mask. The produced signal typically includes a random noise component term that is added to the weighted sum (after the ultrasound waves are physically multiplexed by passage through the active apertures of the mask).

In one example, the weights are selected to indicate whether an active mask element that corresponds to each term of the sum includes an aperture or does not include an aperture. Thus, for example, a weight of 1 indicates the presence of an active aperture within the corresponding mask element, such that the ultrasound that impinges on that mask element is transmitted to the receiver and thus contributes to the total signal. A weight of 0 may indicate the absence of an aperture in the mask element, and no contribution to the total signal. In the example of a phase-inverting element, the corresponding weight value would be −1. In the event that a phase-inverting element also absorbs or otherwise attenuates the ultrasound, the weight value may be adjusted accordingly.

For most of the following discussion, for the sake of simplicity and clarity of the description, the apertures of a coded mask are assumed to lie along at least one linear axis. Thus, the elements of the mask are also assumed to lie along that linear axis. Typically, the center-to-center distance between any two apertures along an axis is approximately equal (e.g., within manufacturing tolerances) to an integral multiple of a minimum separation distance between adjacent apertures. The uniform separation between adjacent elements of the mask is assumed to be equal to this minimum separation distance.

For example, a vector y, each of whose N components represents the multiplexed receiver signal for a different lateral position (e.g., along at least one linear axis parallel to the axis along which the apertures lie) of the coded mask may be represented by:

$$y = Wx + n,$$

where the vector x represents a signal of interest for each active element of the mask (typically including N elements, equal to the number of predetermined lateral positions), W represents an N×N weighting matrix, and n is a vector representing the noise level at each position of the mask. It may be assumed that the components of n are independently and identically distributed random variables, each with zero mean and standard deviation of $\sigma$.

For example, a signal of interest for each element of the mask may be considered to be a signal that would result from transmission of the ultrasound through a single aperture at the corresponding element of the mask. Equivalently, the signal of interest may be considered to be proportional to (e.g., with a ratio determined by properties of the aperture, conversion properties of the receiver, and associated electronics or circuitry) the pressure of the ultrasound that impinges on a single element or active aperture of the mask. In the case of a coded mask where the apertures are arranged along a single dimension, each row of the weighting matrix W may represent a different lateral position of the mask while each column represents an element of the mask. In the example described above, in each row of matrix W corresponding to a lateral position of the mask, the weight value of an element of W is 1 in a column that corresponds to an active element of the mask that includes an active aperture, and 0 in a column that corresponds to an active element of the mask that does not include an aperture. Such a matrix is sometimes referred to as a multiplexing matrix with a spring balance design (as opposed to a chemical balance design with values of 1 corresponding to transmission and −1 corresponding to phase inversion).

As stated above, at each predetermined lateral position of the mask, the lateral positions of the apertures relative to the receiver and to the emitted ultrasound are unique. Therefore, each measured signal component $y_i$ of measured signal vector y, corresponding to the multiplexed signal at one of the predetermined lateral positions of the coded mask, results from a unique multiplexed sampling of the ultrasound. Therefore, the set of measurements that is represented by measured signal vector y may be analyzed to recover the set of measurements of interest x, e.g., within limits imposed by the measurement noise and any other limitations on the accuracy or precision of the measurements.

A vector of recovered signals of interest $\tilde{x}$ may be obtained from the measured signals by applying the inverse $W^{-1}$ of weighting matrix W to the measured signals y:

$$\tilde{x} = W^{-1}y = x + W^{-1}n.$$

The reconstruction error between the recovered signals $\tilde{x}$ and the signals of interest x may be expressed as $$\tilde{x} - x = W^{-1}n.$$

The noise level of the reconstruction may be quantified by the mean square reconstruction error (MSE) given by:

$$MSE = \frac{1}{N}\sqrt{\sum_{i=1}^{N}|\tilde{x} - x|^2}.$$

Given the assumptions stated above regarding the vector n, the noise level for the described multiplexed signals with weighting matrix W may be calculated to be $$MSE_W = \sigma\sqrt{tr[(W^T W)^{-1}]},$$

where T denotes the transpose and tr denotes the trace operation.

The recovered signals may be analyzed, e.g., by tomographic reconstruction or otherwise, to obtain information about the ultrasound source (e.g., heated tissue).

The placement of the apertures on the coded mask may be selected such that the corresponding weighting matrix W (e.g., the weight values in each row of W) may be a variant of a Hadamard matrix. A typical Hadamard matrix H is defined as a square matrix of order N and with values of 1 and −1, satisfying the condition:

$$HH^T = NI_N,$$

where $H^T$ represents the transpose of H, and $I_N$ represents an N×N identity matrix. Apertures of the coded mask may be located along at last one axis of the mask such that the weighting matrix W is a variant of the Hadamard matrix, herein referred to as a cyclic S matrix, where that values of the matrix have values of either 1 (e.g., corresponding to an aperture that is currently located in front of the receiver and thus enables ultrasound to reach the receiver) or 0 (corresponding to a space of the mask that is currently located in front of the receiver but that does not include an aperture and thus blocks ultrasound).

In an example of a cyclic S matrix, the values in each row of the matrix are displaced by one column relative to the preceding row. Since the matrix is cyclic, when the displacement moves a value out of the last column, the value is placed into the first column. Equivalently, the pattern of elements of the mask that include apertures may repeat following the number of elements that are designed to fit in front of the receiver. Typically, the transpose of the matrix is equal to the matrix such that rows and columns are interchangeable.

For example, a quadratic residue construction algorithm, which enables construction of S matrices for any order N in the form of a prime number that is expressible as 4m+3, where m is a natural integer, may be utilized to construct weighting matrix W and the corresponding coded mask. In an example of application of this algorithm, let $a_1, a_2, \ldots, a_N$ represent the remainders of dividing numbers of the form $1, 4, 9, \ldots, ((N-1)/2)^2$ by N (referred to as quadratic residues modulo N). The first row of S may then be constructed by assigning a value of 1 to each element of that row whose index corresponds to one of $a_1, a_2, \ldots, a_N$, while values of other elements are assigned a value of 0. Other rows may then be constructed by cyclically shifting the values of each row by one position relative to the previous row.

Other suitable algorithms may be utilized to generate W and the corresponding coded mask.

To physically implement a cyclic S matrix, a coded mask has at least 2N−1 elements. At each predetermined lateral position of the mask, only N of the elements cover the receiver. The configuration of the covering elements that include active apertures corresponds to a row of the weighting matrix. A lateral shift of the mask by the width of a single element results in a configuration of elements corresponding to a neighboring row of the matrix. In some examples of the coded mask, the number of active apertures is equal to the number of elements of the mask that cover the receiver but do not include an aperture.

In other examples, a mask may be provided for an array of ultrasound detectors (rather than to single receiver as described above). Each element of the mask may then be configured to cover one of the detectors of the array.

A coded aperture ultrasound detector as described herein may be advantageous over other types of ultrasound detectors.

Medical ultrasound imaging, or ultrasonography, conventionally relies on piezoelectric transducers to generate and detect ultrasound. The introduction of transducer arrays has enabled scan-free formation of two dimensional and three dimensional images via electric beam-forming. Since the measurement dataset is limited by the number of transducer elements, it is generally desired to maximize the number of elements to optimize image contrast and resolution. Piezoelectric array transducers have also played a major role in the development of optoacoustic tomography (OAT). The emergence of OAT as a tool for biomedical research and clinical diagnosis leads to new requirements in ultrasound detection that may not always be addressed by piezoelectric technology. In OAT, a wide tomographic view is needed to avoid loss of lateral resolution, whereas conventional linear piezoelectric arrays have acceptance angles of merely ±20 degrees. Use of curved detector arrays may lead to coupling challenges in clinical applications, in which the detectors need to be in close contact with the skin. In addition, since the signals in OAT may be considerably weaker than in ultrasonography, large-area piezoelectric elements may be required so as to maximize sensitivity, thus limiting the number of elements that may be included in the array. Improvement of contrast and reduction of image artifacts may require mechanically scanning of the detector array.

Methods for using a single-element transducer with a rotating random phase mask placed on the transducer surface, or by incorporating acoustic scatterers between the imaged object and the detector array, require advance measurement of the acoustic response of the added element. Placement of a single acoustic aperture in front of a large-area single-element transducer in order to emulate a small-area detector may achieve semi-isotropic detection owing to diffraction and facilitate OAT with a flat transducer, however with significant loss of sensitivity.

On the other hand, use of a coded aperture ultrasound detector as described herein enables measurement of a set of multiplexed signals, enabling the recovery of each signal with a higher sensitivity than the one that may be obtained in a direct measurement using a single aperture. The multiplexing is described by a simple invertible mathematical formula and no advance measurement of the response of the mask is required. The multiplexed measured signal may enable achievement of a greater signal-to-noise ratio (SNR) than would be possible with another technique, e.g., a set of separate detectors. The MSE for direct measurements using a set of N separate detectors, and with the above assumptions regarding noise, would be σ. Thus, the multiplexing advantage G for N multiplexed signals, defined as the calculated SNR of the multiplexed signal divided by the SNR of a direct measurement, may be calculated to be $$G = \{tr[(W^TW)^{-1}]\}^{-1/2}.$$

In the case of cyclic S matrix, the optimal SNR improvement may be $$\sqrt{\frac{(N+1)^2}{4N}} \approx \frac{\sqrt{N}}{2}.$$

FIG. 1A schematically illustrates a one-dimensional coded aperture ultrasound detector, in accordance with an embodiment of the present invention.

Coded aperture ultrasound detector system 10 is configured to detect ultrasound waves 22 that are created by an ultrasound source 20. For example, ultrasound source 20 may include biological tissue or another type of material that is configured to expand and emit ultrasound waves 22 when periodically heated, e.g., by pulses of electromagnetic radiation that are produced by a laser or radiofrequency source, or otherwise. In some cases, e.g., when calibrating or evaluating coded aperture ultrasound detector 10, ultrasound source 20 may include an ultrasound transmitter, e.g., that is connected to an electric pulse generator, electric wave generator, or other operating device.

Coded aperture ultrasound detector system 10 includes ultrasound receiver 12. For example, ultrasound receiver 12 may include a piezoelectric ultrasound transducer or other device that is capable of generating an electric signal that is indicative of the pressure of a portion of ultrasound waves 22 that impinges on a sensitive surface of ultrasound receiver 12.

Signals that are generated by ultrasound receiver 12 may be transmitted by a cabled or wireless connection to processor 18. Processor 18 may include one or more processing units or computers that are configured to perform one or more processing tasks in accordance with programmed instructions. Processor 18 may include or communicate with one or more fixed or removable, volatile or nonvolatile, memory or data storage units for storing one or more of data, parameters, processing results, and programmed instructions. Processor 18 may include or communicate with one or more controllers or control circuitry to control operation of one or more components of coded aperture ultrasound detector system 10.

Processor 18 may include electronics that are configured to perform one or more of sampling, digitizing, or otherwise processing signals that are generated by ultrasound receiver 12. Processor 18 may utilize a memory or data storage device to temporarily or permanently store processed or unprocessed signals that are generated by ultrasound receiver 12.

Coded mask 14 is located between ultrasound source 20 and ultrasound receiver 12, typically as close as possible (e.g., as allowed by mechanical or other constraints) to ultrasound receiver 12. Coded mask 14 includes a plurality of ultrasound apertures 16. Typically, the shapes and sizes of all ultrasound apertures 16 are approximately identical. The size of each ultrasound aperture 16 may be defined by a characterizing dimension, e.g., that is dependent on the shapes of ultrasound apertures 16. For example, the characterizing dimension of an ultrasound aperture 16 may be a diameter (for a circular ultrasound aperture 16, as shown), major axis, length, or other characteristic dimension.

Coded aperture ultrasound detector system 10 includes a translation mechanism for enabling translation of coded mask 14 laterally across ultrasound receiver 12. In FIG. 1A, the translation mechanism is represented by lateral translation arrow 24. The translation mechanism may include one or more controllable motors or actuators for controlled lateral translation of coded mask 14 relative to ultrasound receiver 12. The translation mechanism may include one or more position or motion sensors to monitor the lateral translation of coded mask 14. The translation mechanism may be operated by a controller component or software module of processor 18, or by another controller of coded aperture ultrasound detector system 10.

Processor 18 may be configured to coordinate operation of ultrasound receiver 12 with the translation mechanism. For example, processor 18 may be configured to acquire and store a multiplexed signal when the translation mechanism has translated coded mask 14 to one of a plurality of predetermined positions.

In the example shown, ultrasound apertures 16 are arranged in a single linear row across coded mask 14. Therefore, the translation mechanism that is represented by lateral translation arrow 24 is configured to translate coded mask 14 along at last one axis that is parallel to the row of ultrasound apertures 16. In other examples, ultrasound apertures 16 may be arranged in a two-dimensional arrangement and the translation mechanism may include a two-dimensional stage or other translation mechanism.

Figure 2A:
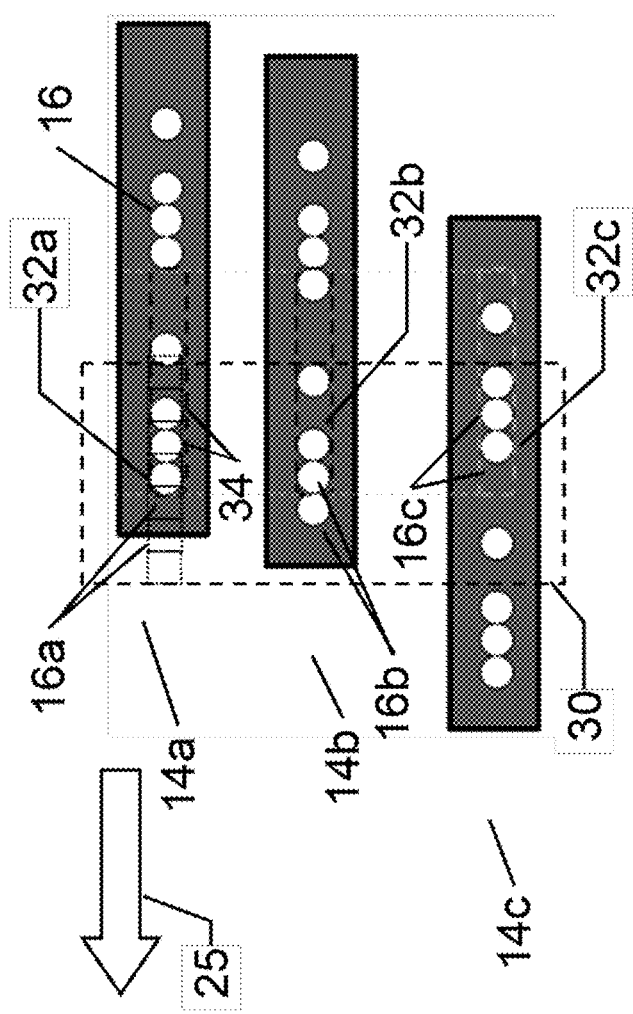
FIG. 2A schematically illustrates scanning of a coded mask over a receiver of a coded aperture ultrasound detector, such as shown in FIG. 1A.

In the example shown, the at last one axis along which ultrasound apertures 16 are arranged may be considered to be divided into a plurality of equally spaced mask elements 34 (FIG. 2A). Some of mask elements 34 include an ultrasound aperture 16, while others do not.

Figure 1B:
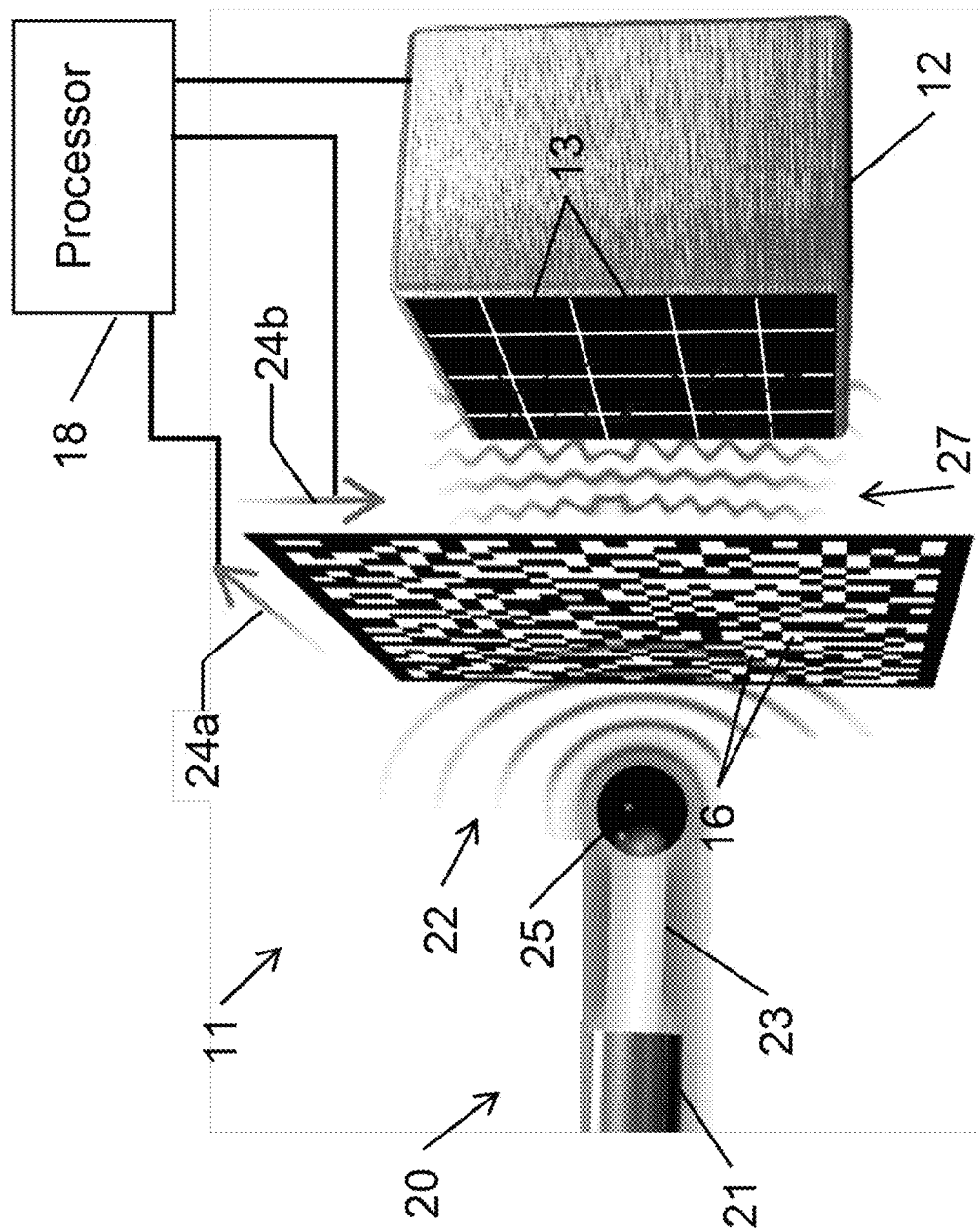
FIG. 1B schematically illustrates a two-dimensional coded aperture ultrasound detector, in accordance with an embodiment of the present invention.

FIG. 1B schematically illustrates a two-dimensional coded aperture ultrasound detector, in accordance with an embodiment of the present invention.

Coded aperture ultrasound detector system 11 is configured to detect ultrasound waves 22 that are created by an ultrasound source 20. In the example shown, ultrasound source 20 includes a target object 25 (e.g., including biological tissue or another type of material) that is configured to expand and emit ultrasound waves 22 when periodically heated, e.g., by pulses of laser beam 23 that are produced by laser 21, or by another pulsed energy source. In some cases, e.g., when calibrating or evaluating coded aperture ultrasound detector 10, ultrasound source 20 may include an ultrasound transmitter, e.g., that is connected to an electric pulse generator, electric wave generator, or other operating device.

Coded aperture ultrasound detector system 10 includes ultrasound receiver 12. For example, ultrasound receiver 12 may include a piezoelectric ultrasound transducer or other device that is capable of generating an electric signal that is indicative of the pressure of a portion of ultrasound waves 27 that impinges on a sensitive surface of ultrasound receiver 12. In the example shown, ultrasound receiver 12 includes a square array of ultrasound transducers 13. In other examples, ultrasound receiver 12 may include another arrangement of ultrasound transducers 13, or a single ultrasound transducer.

Signals that are generated by ultrasound receiver 12 may be transmitted by a cabled or wireless connection to processor 18.

Coded mask 14 is located between ultrasound source 20 and ultrasound receiver 12, typically as close as possible (e.g., as allowed by mechanical or other constraints) to ultrasound receiver 12. Coded mask 14 includes a plurality of ultrasound apertures 16. Typically, the shapes and sizes of all ultrasound apertures 16 are approximately identical. The size of each ultrasound aperture 16 may be defined by a characterizing dimension, e.g., that is dependent on the shapes of ultrasound apertures 16. For example, the characterizing dimension of an ultrasound aperture 16 may be a length of a side (for square ultrasound apertures 16, as shown), diameter, major axis, or other characteristic dimension.

Coded aperture ultrasound detector system 10 includes a translation mechanism for enabling translation of coded mask 14 laterally across ultrasound receiver 12. In FIG. 1B, a two-dimensional translation mechanism is represented by lateral translation arrows 24a and 24b. The translation mechanism may include one or more controllable motors or actuators for controlled lateral translation of coded mask 14 relative to ultrasound receiver 12. The translation mechanism may include one or more position or motion sensors to monitor the lateral translation of coded mask 14. The translation mechanism may be operated by a controller component or software module of processor 18, or by another controller of coded aperture ultrasound detector system 10.

Processor 18 may be configured to coordinate operation of ultrasound receiver 12 with the translation mechanism. For example, processor 18 may be configured to acquire and store a multiplexed signal when the translation mechanism has translated coded mask 14 to one of a plurality of predetermined positions.

In the example shown, ultrasound apertures 16 are arranged in a two-dimensional square array across coded mask 14. Therefore, the translation mechanism that is represented by lateral translation arrows 24a and 24b is configured to translate coded mask 14 along perpendicular axes that are each parallel to one of the dimensions of the square array of ultrasound apertures 16. For example, the translation mechanism may include a two-dimensional stage or other two-dimensional translation mechanism. In other examples, ultrasound apertures 16 may be arranged in a rectangular or other two-dimensional arrangement.

FIG. 2A schematically illustrates scanning of a one-dimensional coded mask over a receiver of a coded aperture ultrasound detector, such as shown in FIG. 1A.

In the example of a cyclic coded mask 14 that is shown (which, for the sake of clarity and simplicity of the present discussion, is selected to have an order of N=7 which may be a lower order than that of a typical coded mask 14), the pattern of mask elements 34 that do and do not include ultrasound apertures 16 is repeated after seven mask elements 34. In order to provide a cyclic pattern, the total number of mask elements 34 is 13 (=2N−1) such that there are always seven active mask elements 34 that cover ultrasound receiver 12.

In the example shown, coded mask 14 is initially (e.g., at the time of a first acquisition of signals from ultrasound receiver 12) at mask position 14a. Box 30 indicates the constant position of ultrasound receiver 12 as coded mask 14 is translated between signal acquisitions in the direction indicated by translation arrow 25. Thus, when coded mask 14 is at mask position 14a, the seven mask elements 34 of mask element region 32a, which includes four active apertures 16a, cover ultrasound receiver 12.

Figure 2B:
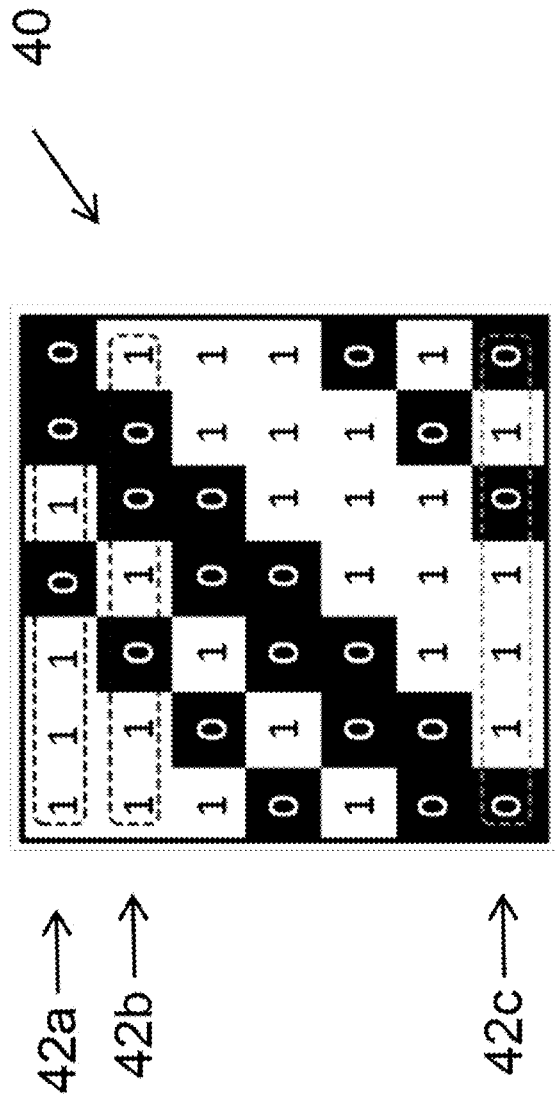
FIG. 2B illustrates a weighting matrix corresponding to the scanned coded mask shown in FIG. 2A.

FIG. 2B illustrates a weighting matrix corresponding to the scanned coded mask shown in FIG. 2A.

When coded mask 14 is at mask position 14a, the arrangement of apertures 16a in mask element region 32a corresponds to the values in row 42a of weighting matrix 40. In row 42a, values of 1 correspond to the positions of active apertures 16a, and values of 0 correspond to the positions of mask elements 34 within mask element region 32a that do not include apertures.

A translation of coded mask 14 by one mask element 34 in the direction of translation arrow 25 brings coded mask 14 to mask position 14b. At mask position 14b, the seven mask elements 34 of mask element region 32a, which include four active apertures 16b, cover ultrasound receiver 12. The values of row 42b of weighting matrix 40 correspond to mask element region 32b.

In the 7$^{th}$ order example shown, five further translations of coded mask 14, each by one mask element 34, in the direction of translation arrow 25 bring coded mask 14 to final mask position 14c. At mask position 14c, the seven mask elements 34 of mask element region 32c, which include four active apertures 16c, cover ultrasound receiver 12. The values of row 42c of weighting matrix 40 correspond to mask element region 32c.

It may be noted that at each position of coded mask 14 between mask position 14a and mask position 14c, the pattern of mask elements 34, and thus of values in the rows of weighting matrix 40, are unique. Any further translation of coded mask 14 would cause the pattern to repeat, and is thus cyclic. Thus, the acquired multiplexed signal at each lateral position of coded mask 14 samples a different portion of ultrasound waves 22. It may be further noted that in the example shown, the number of active ultrasound apertures 16 that cover ultrasound receiver 12 is identical at all positions of coded mask 14.

Figure 3:
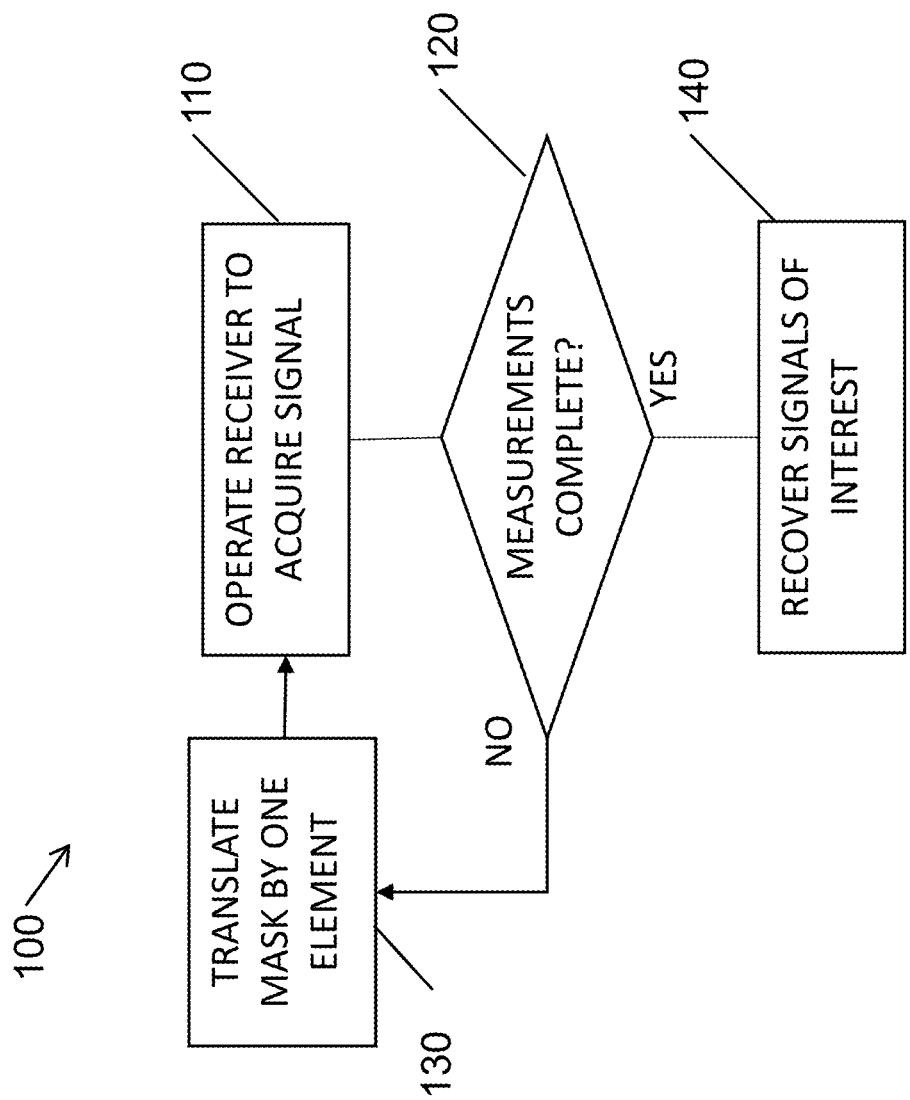
FIG. 3 is a flowchart depicting an ultrasound detection method, in accordance with an embodiment of the present invention.

FIG. 3 is a flowchart depicting an ultrasound detection method, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Ultrasound detection method 100 may be performed by processor 18 of coded aperture ultrasound detector system 10. Ultrasound detection method 100 may be executed in response to a control command that is generated by an operator of coded aperture ultrasound detector system 10, automatically or periodically, or otherwise.

Ultrasound receiver 12 may be operated to acquire an ultrasound signal (block 110). The acquired ultrasound signal is typically a multiplexed signal resulting by concurrent transmission of ultrasound waves 22 via active ultrasound apertures to ultrasound receiver 12.

The number of multiplexed measurements that have been acquired at different positions of coded mask 14 may be compared with a total number of required measurements (block 120). Typically the required number of measurements is equal to the number (N) of mask elements 34 of coded mask 14. In other examples, measurements may be acquired only during some of the possible lateral positions of coded mask 14.

If more measurements are required, coded mask 14 may be translated by (e.g., the width of) one mask element (block 130). Ultrasound receiver 12 may then be operated to acquire another multiplexed signal at the new position of coded mask 14 (returning to block 110).

If all measurements have been completed, the acquired signals may be processed as described above in order to recover the signals of interest (block 140). In the case where measurements are not acquired at all positions of coded mask 14, the algorithm may be modified in order to enable recovery of all of the signals of interest.

Results of laboratory measurements by application of ultrasound detection method 100 using an example of coded mask 14 are described below.

Figure 4A:
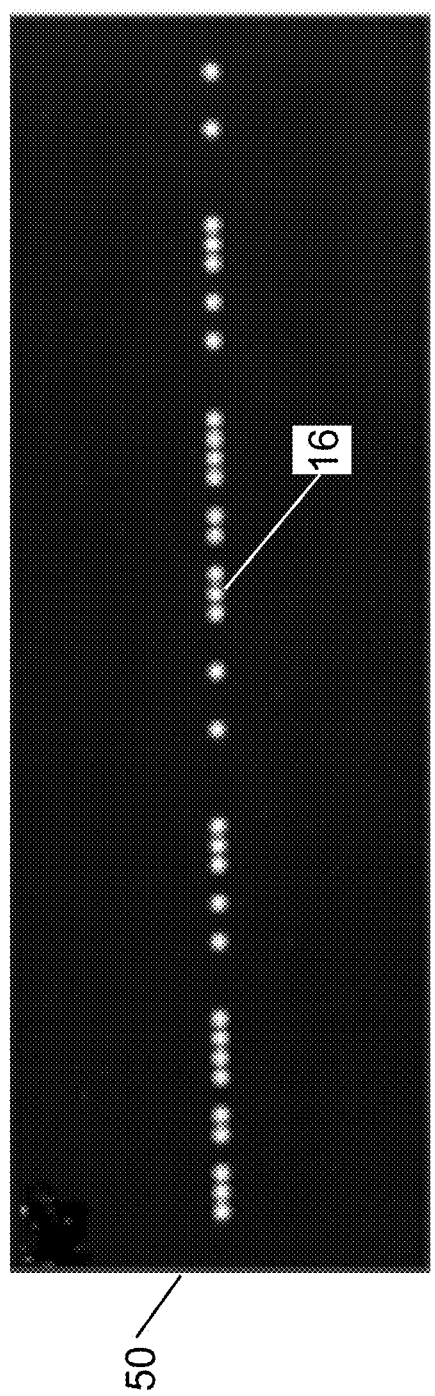
FIG. 4A schematically illustrates an example of a coded mask, in accordance with an embodiment of the invention.
Figure 4B:
FIG. 4B schematically illustrates a weighting matrix corresponding to the coded mask shown in FIG. 4A.
Figure 4C:
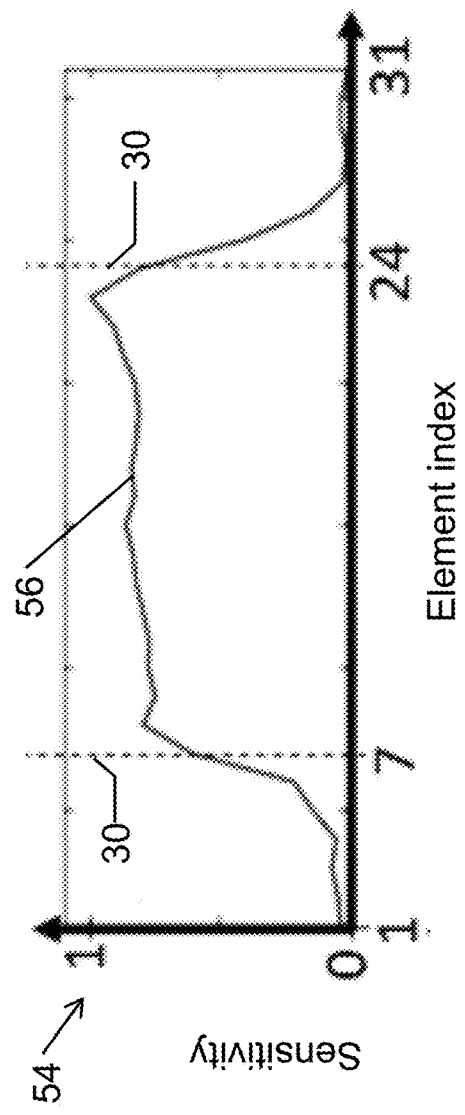
FIG. 4C represents results of a sensitivity measurement using the coded mask shown in FIG. 4A.
Figure 4D:
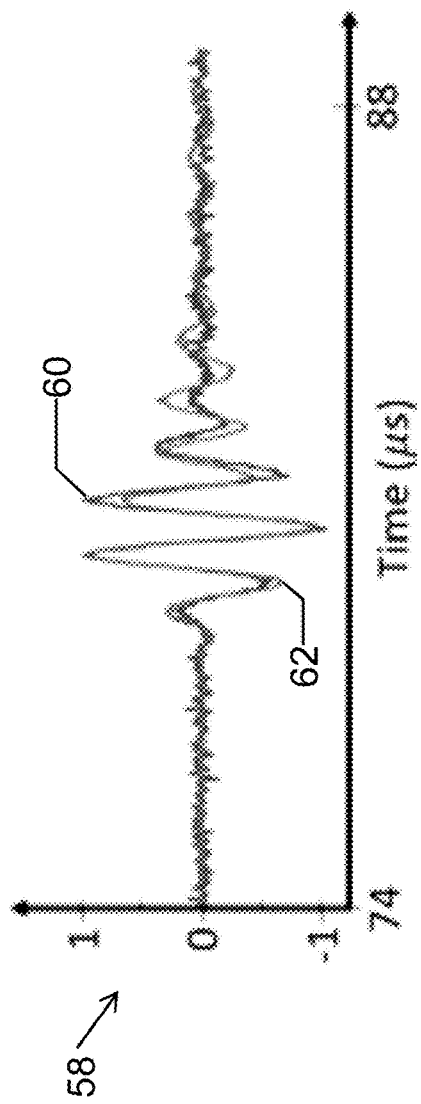
FIG. 4D compares waveform measurements using a signal multiplexed via the coded mask shown in FIG. 4A and using a detector with a single aperture.
Figure 4E:
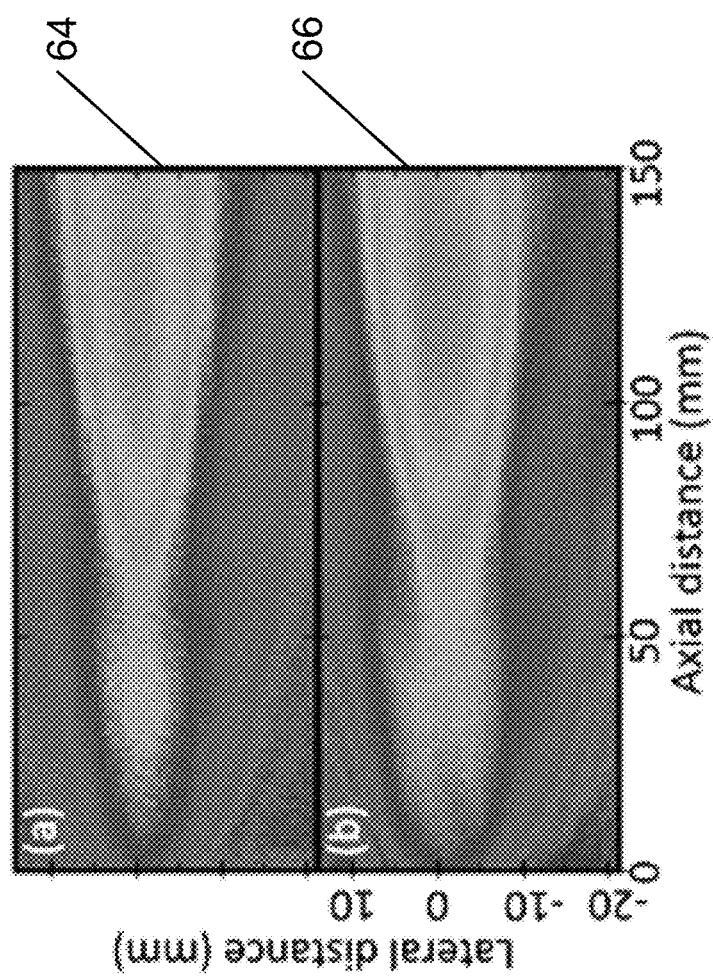
FIG. 4E compares transmitter emission pattern measurements using a signal multiplexed via the coded mask shown in FIG. 4A and using a detector with a single aperture.

FIG. 4A schematically illustrates an example of a coded mask, in accordance with an embodiment of the invention. FIG. 4B schematically illustrates a weighting matrix corresponding to the coded mask shown in FIG. 4A. FIGS. 4C-4E represent results of measurements made with the coded mask shown in FIG. 4A.

Coded mask 50 includes a pattern of 31 linearly arranged mask elements. In representation 52 of the cyclic S matrix corresponding to coded mask 50, white squares correspond to positions of active ultrasound apertures 16 (corresponding to values of 1), and black squares correspond to elements of coded mask 50 that do not include apertures (corresponding to values of 0).

For the measurements whose results are represented in the graphs in FIGS. 4C-4E, coded mask 50 was constructed of a 0.53 mm layer of PORON 4701-30-25 foam bounded to a 1 mm thick polymethyl-methacrylate (PMMA) backing plate. Ultrasound apertures 16 were produced by laser cutting, each with a diameter of 1.5 mm, where the distance between the centers of adjacent mask elements was 2 mm, corresponding to a virtual detector array detector of length 61.5 mm.

For the sake of laboratory measurements, ultrasound source 20 included an ultrasound transmitter connected to an electric pulse generator and operating at 1 MHz. The diameter of ultrasound receiver 12 was 38 mm. The measurements were performed inside a water tank.

FIG. 4C represents results of a sensitivity measurement using the coded mask shown in FIG. 4A.

Sensitivity graph 54 includes a sensitivity curve 56 showing the relative recovered signals ($\tilde{x}$), or virtual detector sensitivity, at each mask element 34 of coded mask 50. The size of ultrasound receiver 12 relative to coded mask 50 and sensitivity curve 56 is indicated by outlines of box 30. Sensitivity curve 56 may be utilized to calibrate the virtual detectors. Sensitivity curve 56 indicates that the response of the virtual detectors decreases for element indices outside the receiver span. While one might expect that all the virtual detectors outside the span of the receiver would receive a zero signal, a gradual decline in sensitivity outside the receiver span is seen. Since the aperture diameter is comparable to the acoustic wavelength, the transmission through the aperture is semi-isotropic. It is therefore expected that some of the acoustic radiation from array elements that do not cover by the receiver would still reach the receiver.

FIG. 4D compares waveform measurements using a signal multiplexed via the coded mask shown in FIG. 4A and using a detector with a single aperture.

In waveform graph 58, the relative amplitudes of single aperture signal 60 and multiplexed signal 62 are similar. However, the indicated noise of single aperture signal 60 is noticeably greater than that of multiplexed signal 62.

FIG. 4E compares transmitter emission pattern measurements using a signal multiplexed via the coded mask shown in FIG. 4A and using a detector with a single aperture.

Single aperture field map 64 is a map of relative acoustic field magnitude (as indicated by the shading) at different positions (lateral displacement and axial distance) relative to the transmitter ultrasound source as measured by a single aperture detector. Multiplexed field map 66 shows the same acoustic field as measured by signal multiplexed via coded mask 50. It may be noted that the maps are similar. However, the noise of single aperture field map 64, as manifested by the blurriness at the boundaries between differently shaded regions, is noticeably greater than that of multiplexed field map 66.

Figure 4F:
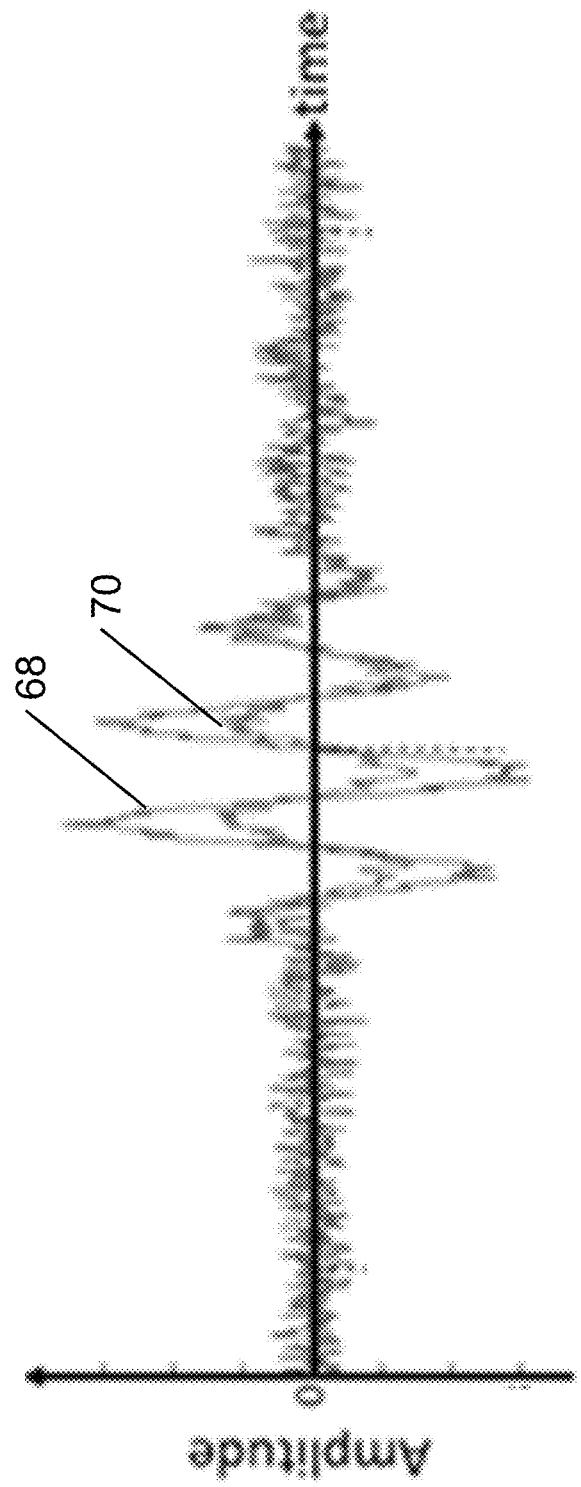
FIG. 4F compares waveform measurements with the coded mask shown in FIG. 4A when the direction of transmission by the ultrasound source is rotated relative to the axis of the receiver.

FIG. 4F compares waveform measurements with the coded mask shown in FIG. 4A when the direction of transmission by the ultrasound source is rotated relative to the axis of the receiver.

Waveform signal 68 shows the signal when the direction of ultrasound transmission is along the axis of ultrasound receiver 12. Waveform signal 70 shows the signal when the direction of ultrasound transmission is at an angle of 40° to the axis of ultrasound receiver 12. As shown, when the ultrasound transmission is at the oblique incidence angle, the signal was attenuated by 6.5 dB.

In some embodiments, the present disclosure provides for optoacoustic tomography (OAT) which uses an acoustic mask with coded apertures and a flat piezoelectric detector to create a virtual detector array with (i) high angular acceptance achieved by diffraction from the apertures, and (ii) high sensitivity, achieved by multiplexing the signals from all apertures.

Using this approach, a 2D virtual array with 1763 elements may be created, where the signal for each virtual element is obtained by applying a linear transformation on the measured data. The disclosed virtual array setup was studied in an experiment by performing OAT of a complex 3D object, achieving axial and lateral resolutions of 150 μm and 500 μm in a flat detection geometry, and providing image quality comparable to that achieved with curved detection geometries. In terms of sensitivity, the present approach led to a 21-fold gain in the measurement SNR in comparison to a single detector with the same size of a single element of our virtual array.

As noted above, in OAT, piezoelectric transducer arrays are used to detect the acoustic signals generated by the imaged specimen. Those arrays face challenges of insufficient SNR, due to weak acoustic signals common in OAT, necessitating the use of large area detectors and limiting element count in arrays. Current OAT systems employ up to 512 elements and often require scanning to achieve sufficient visual quality.

Accordingly, in some embodiments, the present disclosure provides for a spatial coding method via a 2D cyclic, optimal Hadamard mask. The disclosed method was validated by performing OAT with a virtual 41×43 2D array.

Figure 5A:
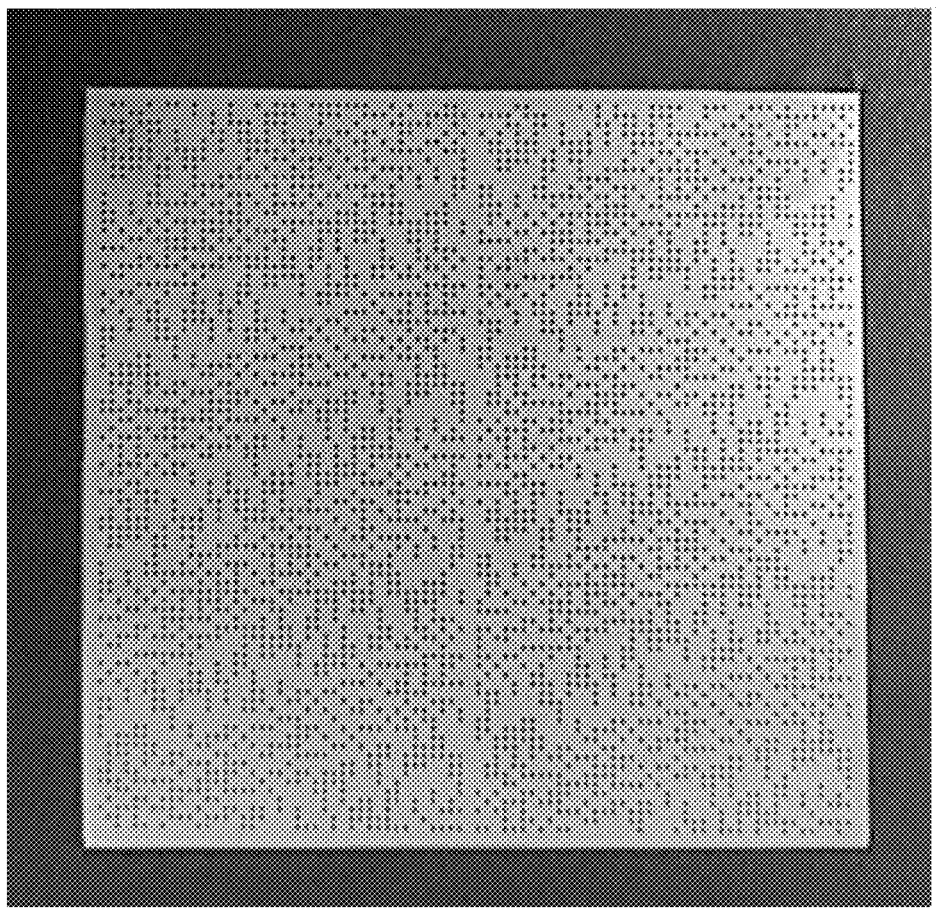
FIG. 5A shows an exemplary coded mask used in an experiment conducted by the present inventors.

With reference back to FIG. 1B, an experimental setup of the present disclosure was used to evaluate the present disclosure, OAT measurements were performed, mapping the acoustic fields by a single detector, masked with a Hadamard coded aperture scanned in x-y plane. A cyclic coded pattern was manufactured, coding a single detector into N=1763 virtual elements arranged in $N_p \times N_Q = 41 \times 43$ 2D formation. FIG. 5A shows an exemplary coded mask used in the experiment. The mask comprises circular apertures with 0.5 mm diameter that are laser cut through a 0.3 mm wide stainless-steel plate with 1 mm spacing between their centers. Unused mask areas were coated with 0.53 mm thick foam layer (4701-30-25, PORON) to reduce reflections. Laser pulses at 720 nm, with 34 mJ power were generated at a 100 Hz rate (SpitLight DPSS EVO I OPO, InnoLas Laser). FIG. 5C shows the imaged object illuminated by the pulses—a knot made from 200 μm thick coper wire coated with Indian ink.

The coded mask was placed 24 mm from the object and scanned in x-y plane by 2 stages (M-414.32S & M-403.6PD, PI) with 1 mm steps through N discrete positions. Few millimeters after the mask, a single, unfocused transducer (I8-0518-R, Olympus) was placed, with 28.6 mm diameter, 5 MHz central frequency and 3.1-6.5 MHz 3 dB BW. The detected signals passed through a 1-20 MHz filter, were amplified by 20 dB (DHPVA, Femto) and sampled with 4 samples averaging per acquisition (DSOX4154A, Keysight).

After performing N consecutive measurements, the acoustic fields were un-multiplexed from the multiplexing measurement by $$\hat{X}_{N \times t} = S_{N \times N}^{-1} Y_{N \times t},$$

where $Y_{N \times t}$ is the measurements matrix, $S_{N \times N}^{-1}$ is the invert of the multiplexing matrix and $\hat{X}_{N \times t}$ are the recovered un-multiplexed signals, reshaped to $X_{N \times N \times t}$ signals matrix. This measurement was repeated 4 times with 0.5 mm offsets to the masks starting position in each direction (x–y) to achieve a full sampling grid and avoid under sampling artifacts. The interlaced acoustic signals from those 4 measurements achieved a total of 7052 signals, mapping the acoustic field with 82×86 virtual circular elements with 0.5 mm diameter and spacing between them. 3D optical absorption map was recovered from the un-multiplexed signals by applying Optoacoustic back projection algorithm as in regular OAT with a single exception of shifting the time vector by the delay from the mask to the detector, since the imaging plane is the grid plane.

Figure 5B:
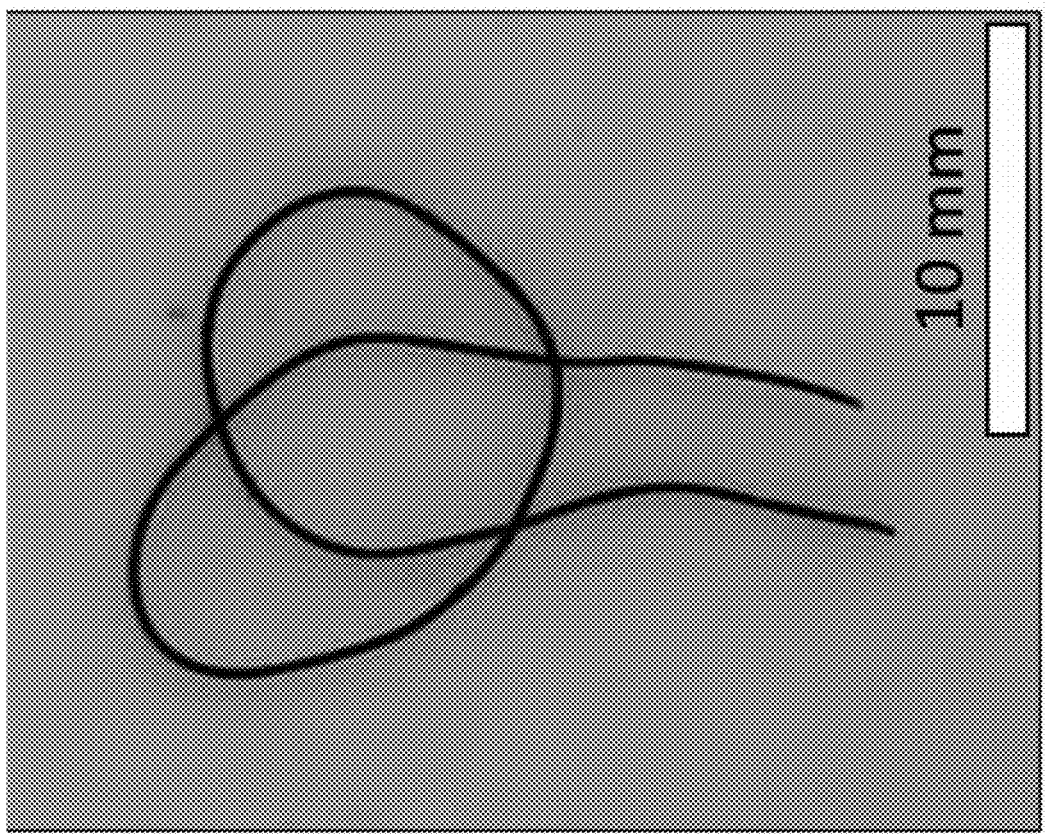
FIG. 5B shows the imaged object used in an experiment conducted by the present inventors.
Figure 6A:
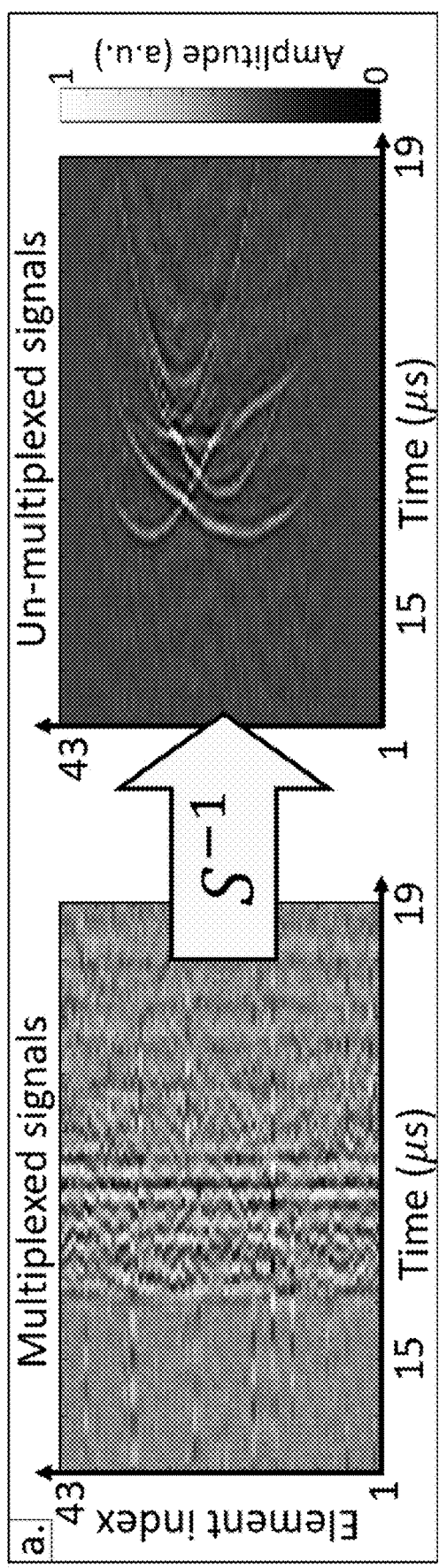
FIG. 6A shows Optoacoustic Tomography (OAT) results for the imaged object in FIG. 5B.
Figure 6B:
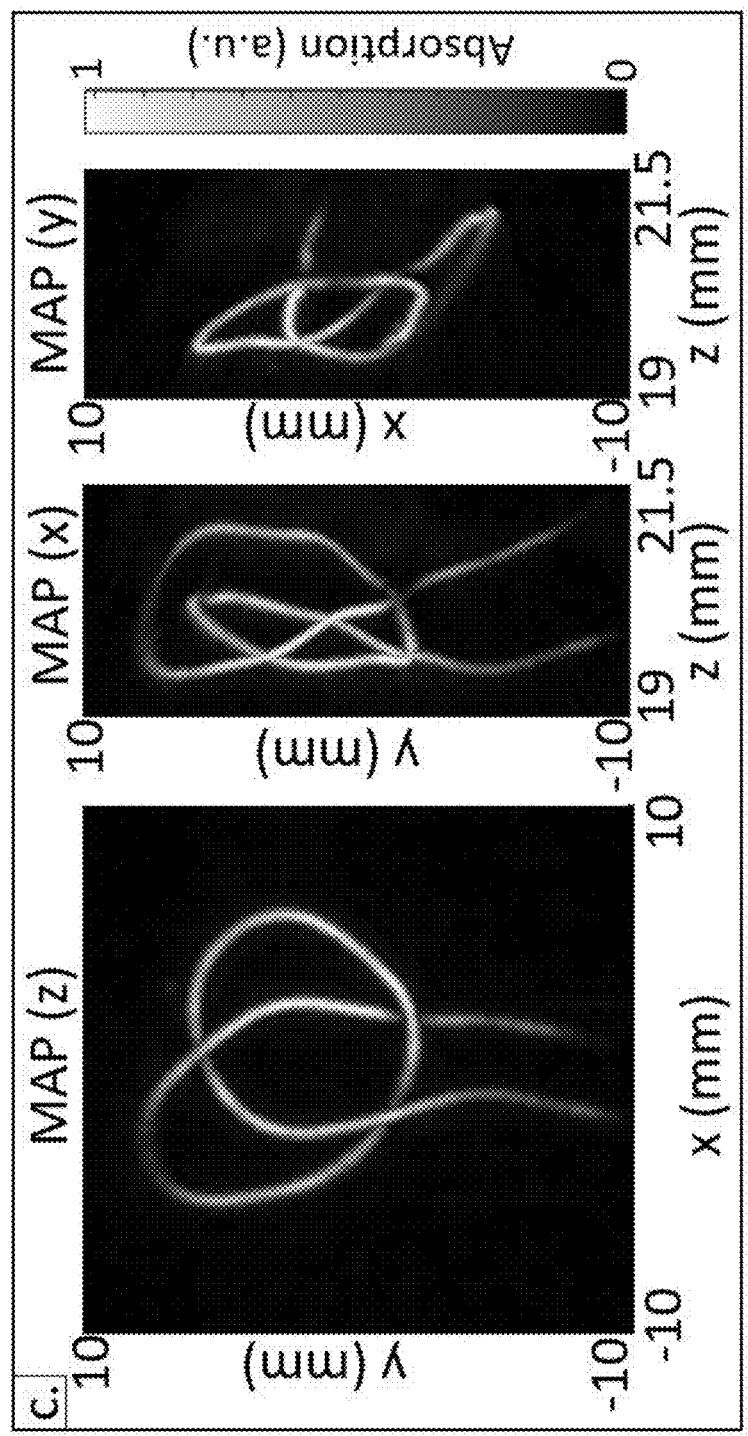
FIG. 6B shows map projections of the reconstructed 3D optical absorption map.

FIG. 6A shows OAT results for the imaged coper wire object shown in FIG. 5B. Shown is a cross section for x=0 mm of the measured, multiplexed and analytically un-multiplied acoustic signals. FIG. 6B shows map projections of the reconstructed 3D optical absorption map.

In some embodiments, the present disclosure provides for a novel approach to detect acoustic signals by coding a flat detector with a spatially filtering acoustic mask. The present method was experimentally demonstrated by OAT of a complex 3D object with a virtual 2D detection array of 1763 elements. The present method achieved axial and lateral resolutions of 150 µm and 500 µm, with imaging quality comparable to the one achieved by curved detection geometries and a 21-fold gain in the measurement SNR in comparison to a single detector with the size of a single element of our virtual array. The present method requires no prior calibration, is cost effective, modular and provides postproduction flexibility with the virtual array geometry. The present further has potential for high frequency detection arrays which are currently technologically limited for pitches below 100 um, because apertures manufacturing at this scale should be significantly simpler. Furthermore, parallelization of our detection method can transform each element of a detection array into its own virtual detection arrays, reaching extremely high element counts above $10^5$.

The invention claimed is:

1. An ultrasound detection device comprising:
an ultrasound receiver configured to generate a signal indicative of a pressure of ultrasound that impinges on the receiver; and
a coded mask comprised of an ultrasound-blocking material perforated by an array of a plurality of apertures,
wherein said coded mask comprises a plurality of mask elements, selected from (i) elements comprising an aperture of the plurality of apertures, via which ultrasound is transmitted, and (ii) elements that are opaque to ultrasound, and
wherein the apertures are arranged such that when the coded mask is placed over the receiver between the receiver and a source of ultrasound in a predetermined lateral position of a plurality of predetermined lateral positions, the ultrasound is transmitted from the ultrasound source to the receiver via a known unique pattern of active apertures of the plurality of apertures, said pattern is unique to the predetermined lateral position, such that the signal that is generated by the receiver is a multiplexed signal.

2. The device of claim 1, wherein said coded mask is laterally translatable relative to the receiver to a plurality of predetermined lateral positions.

3. The device of claim 2, wherein the number of active apertures via which the ultrasound is transmitted to the receiver is identical at each of the plurality of predetermined lateral positions.

4. The device of claim 1, wherein said coded mask and said receiver are laterally translatable together to a plurality of lateral positions, and wherein said coded mask remains stationary relative to the receiver during said translating.

5. The device of claim 1, wherein the plurality of apertures are arranged along at least one axis, and wherein the separation distance between any pair of the apertures along each of said at least one axis is substantially equal to an integral multiple of a minimum separation distance between adjacent apertures of the plurality of apertures.

6. The device of claim 5, wherein the plurality of apertures are arranged along the at least one axis such that when the coded mask is divided along each of the at least one axis into a plurality of elements, the length of each of the elements is substantially equal to the minimum separation distance, and wherein the pattern of the active apertures within those elements of the coded mask that cover the receiver corresponds to values in a row of a weighting matrix in the form of a cyclic Hadamard S matrix.

7. The device of claim 1, wherein the plurality of apertures are arranged in a two-dimensional array.

8. The device of claim 1, further comprising a processor that is configured to process the multiplexed signals to recover an acoustic signal of interest, and wherein the processor is configured to process the multiplexed signals by applying an inverse of a weighting matrix in the form of a cyclic Hadamard S matrix, that corresponds to the unique patterns of the active apertures.

9. An ultrasound detection method comprising:
placing a coded mask relative to an ultrasound receiver in a predetermined lateral position, the coded mask comprised of an ultrasound blocking material perforated by an array of a plurality of apertures,
wherein said coded mask comprises a plurality of mask elements, selected from (i) elements comprising an aperture of the plurality of apertures, via which ultrasound is transmitted, and (ii) elements that are opaque to ultrasound, and
wherein the apertures are arranged such that the ultrasound is transmitted from an ultrasound source to the receiver via a unique pattern of active apertures of the plurality of apertures, said pattern is unique to the predetermined lateral position;
operating the ultrasound receiver to acquire a multiplexed signal; and
processing the acquired multiplexed signals to recover a signal of interest.

10. The method of claim 9, wherein said coded mask and said receiver are laterally translatable together to a plurality of lateral positions, and wherein said coded mask remains stationary relative to the receiver during said translating.

11. The method of claim 9, wherein said coded mask is translatable relative to the receiver to each of a plurality of predetermined lateral positions, and wherein said method comprises sequentially laterally translating said coded mask relative to said ultrasound receiver to each of said plurality of predetermined lateral positions.

12. The method of claim 9, wherein the plurality of apertures are arranged along two or more axes, and wherein the separation distance along each of the two or more axes between any pair of the apertures is substantially equal to an integral multiple of a minimum separation distance between adjacent apertures of the plurality of apertures.

13. The method of claim 12, wherein said coded mask is translatable relative to the receiver to each of a plurality of predetermined lateral positions, wherein said method comprises sequentially laterally translating said coded mask relative to said ultrasound receiver to each of said plurality of predetermined lateral positions, and wherein the displacement of each translation being substantially equal to the minimum separation distance.

14. The method of claim 9, wherein processing the multiplexed signals comprises applying an inverse of a weighting matrix in the form of a cyclic Hadamard S matrix to the multiplexed signals.

15. The method of claim 14, wherein, when the plurality of apertures are arranged along at least one axis, wherein each weight value in a row of the weighting matrix is indicative of the presence or absence of an active aperture in an active element of the coded mask that is located between the ultrasound source and the receiver, wherein a width of each active element is substantially equal to a minimum separation between two of the apertures along each of the at least one axis, and wherein the weight values in each successive row of the weighting matrix corresponds to the presence or absence of active apertures.

16. The method of claim 15, wherein a value in a row of the weighting matrix that corresponds to the presence of an active aperture is 1, and a value in a row of the weighting matrix that corresponds to the absence of an active aperture is 0.

17. The method of claim 9, wherein the ultrasound source comprises heated biological tissue, wherein said heating spatially varies thermal expansion within the tissue which induces ultrasound waves.

18. The device of claim 1, wherein each aperture is equal to, or on the order of a characteristic wavelength of the transmitted ultrasound, and wherein a maximum distance between the mask and the receiver is selected to limit a diffractive spreading of the ultrasound transmission to a predefined range.

* * * * *